(12) United States Patent
Wack et al.

(10) Patent No.: US 8,475,520 B2
(45) Date of Patent: Jul. 2, 2013

(54) STENTING RING WITH MARKER

(75) Inventors: Thilo Wack, Durmersheim (DE); Wolfgang Supper, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 271 days.

(21) Appl. No.: 12/517,096

(22) PCT Filed: Dec. 5, 2007

(86) PCT No.: PCT/EP2007/063347
§ 371 (c)(1),
(2), (4) Date: Jun. 1, 2009

(87) PCT Pub. No.: WO2008/068279
PCT Pub. Date: Jun. 12, 2008

(65) Prior Publication Data
US 2010/0070021 A1 Mar. 18, 2010

(30) Foreign Application Priority Data
Dec. 6, 2006 (GB) .................................... 0624419.8

(51) Int. Cl.
*A61F 2/91* (2013.01)
(52) U.S. Cl.
USPC ........................................................ 623/1.34
(58) Field of Classification Search
USPC ........................................ 623/1.34, 1.32, 1.44
See application file for complete search history.

(56) References Cited

U.S. PATENT DOCUMENTS

| 5,091,205 A | 2/1992 | Fan |
| 5,464,419 A | 11/1995 | Glastra |

(Continued)

FOREIGN PATENT DOCUMENTS

| DE | 04130431 A1 | 3/1993 |
| DE | 29621207 U1 | 1/1997 |

(Continued)

OTHER PUBLICATIONS

EP 07802603.6 filed Aug. 14, 2007 Office Action dated Dec. 13, 2010.

(Continued)

*Primary Examiner* — Thomas J Sweet
*Assistant Examiner* — Cheryl Miller
(74) *Attorney, Agent, or Firm* — Rutan & Tucker, LLP

(57) ABSTRACT

A stenting ring made of a tube or rolled-up sheet that has a characteristic wall thickness. The ring defines a lumen and is equipped with at least one marker made of a material different from that of the ring. The ring is expansible from a radially compact disposition with a relatively small circumference to a radially expanded disposition with a relatively large circumference. The ring exhibits in the compact disposition a serpentine arrangement of succeeding struts lying in alternate opposite directions to the longitudinal axis of the lumen. The marker has a thickness in the radial direction of the ring that is less than the characteristic wall thickness, and has a width that extends circumferentially around an arc of the ring. The marker is attached to the ring at a zone located at a point intermediate in the extent of said arc. The marker overlaps with a respective one of said struts, at each end of its circumferential arc, when the ring is in the compact disposition, the respective struts moving away from each other, and from the marker, when the ring expands towards said radially expanded disposition.

16 Claims, 2 Drawing Sheets

U.S. PATENT DOCUMENTS

| | | | |
|---|---|---|---|
| 5,527,353 A | 6/1996 | Schmitt | |
| 5,591,223 A | 1/1997 | Lock et al. | |
| 5,645,532 A | 7/1997 | Horgan | |
| 5,725,572 A | 3/1998 | Lam et al. | |
| 5,741,327 A | 4/1998 | Frantzen | |
| 5,759,192 A | 6/1998 | Saunders | |
| 5,800,511 A | 9/1998 | Mayer | |
| 5,824,042 A | 10/1998 | Lombardi et al. | |
| 5,824,059 A | 10/1998 | Wijay | |
| 5,824,077 A | 10/1998 | Mayer | |
| 5,843,118 A | 12/1998 | Sepetka et al. | |
| 5,858,556 A | 1/1999 | Eckert et al. | |
| 5,861,027 A | 1/1999 | Trapp | |
| 5,868,783 A | 2/1999 | Tower | |
| 5,922,020 A | 7/1999 | Klein et al. | |
| 6,022,374 A | 2/2000 | Imran | |
| 6,053,940 A | 4/2000 | Wijay | |
| 6,056,187 A | 5/2000 | Acciai et al. | |
| 6,086,611 A | 7/2000 | Duffy et al. | |
| 6,099,561 A | 8/2000 | Alt | |
| 6,102,938 A * | 8/2000 | Evans et al. | 623/1.35 |
| 6,174,329 B1 | 1/2001 | Callol et al. | |
| 6,241,762 B1 | 6/2001 | Shanley | |
| 6,270,524 B1 | 8/2001 | Kim | |
| 6,293,966 B1 | 9/2001 | Frantzen | |
| 6,312,456 B1 | 11/2001 | Kranz et al. | |
| 6,334,871 B1 | 1/2002 | Dor et al. | |
| 6,355,057 B1 | 3/2002 | DeMarais et al. | |
| 6,379,381 B1 | 4/2002 | Hossainy et al. | |
| 6,387,123 B1 | 5/2002 | Jacobs et al. | |
| 6,409,752 B1 | 6/2002 | Boatman et al. | |
| 6,451,047 B2 | 9/2002 | McCrea et al. | |
| 6,471,721 B1 | 10/2002 | Dang | |
| 6,475,233 B2 | 11/2002 | Trozera | |
| 6,478,816 B1 | 11/2002 | Kveen et al. | |
| 6,540,777 B2 | 4/2003 | Stenzel et al. | |
| 6,547,818 B1 | 4/2003 | Rourke et al. | |
| 6,562,065 B1 | 5/2003 | Shanley | |
| 6,585,757 B1 | 7/2003 | Callol | |
| 6,605,110 B2 | 8/2003 | Harrison | |
| 6,629,994 B2 | 10/2003 | Gomez et al. | |
| 6,676,700 B1 | 1/2004 | Jacobs et al. | |
| 6,770,089 B1 | 8/2004 | Hong et al. | |
| 6,797,217 B2 | 9/2004 | McCrea et al. | |
| 6,827,734 B2 | 12/2004 | Fariabi | |
| 6,878,162 B2 | 4/2005 | Bales et al. | |
| 6,979,346 B1 | 12/2005 | Hossainy et al. | |
| 7,060,093 B2 | 6/2006 | Dang et al. | |
| 7,135,038 B1 | 11/2006 | Limon | |
| 7,175,654 B2 | 2/2007 | Bonsignore et al. | |
| 7,462,190 B2 | 12/2008 | Lombardi | |
| 7,468,071 B2 | 12/2008 | Edwin et al. | |
| 7,479,157 B2 | 1/2009 | Weber et al. | |
| 7,691,461 B1 | 4/2010 | Prabhu | |
| 7,771,463 B2 | 8/2010 | Ton et al. | |
| 7,772,659 B2 | 8/2010 | Rodmacq et al. | |
| 8,043,364 B2 | 10/2011 | Lombardi et al. | |
| 8,043,366 B2 * | 10/2011 | Brown et al. | 623/1.35 |
| 8,152,842 B2 | 4/2012 | Schlun | |
| 8,322,593 B2 | 12/2012 | Wack | |
| 2002/0007212 A1 | 1/2002 | Brown et al. | |
| 2002/0116044 A1 | 8/2002 | Cottone et al. | |
| 2002/0116051 A1 | 8/2002 | Cragg | |
| 2002/0138136 A1 * | 9/2002 | Chandresekaran et al. | 623/1.34 |
| 2002/0193867 A1 | 12/2002 | Gladdish et al. | |
| 2002/0193869 A1 * | 12/2002 | Dang | 623/1.15 |
| 2002/0198589 A1 | 12/2002 | Leong | |
| 2003/0055485 A1 | 3/2003 | Lee et al. | |
| 2003/0135254 A1 | 7/2003 | Curcio et al. | |
| 2003/0144725 A1 | 7/2003 | Lombardi | |
| 2003/0216807 A1 | 11/2003 | Jones et al. | |
| 2003/0225448 A1 | 12/2003 | Gerberding | |
| 2004/0015228 A1 | 1/2004 | Lombardi et al. | |
| 2004/0015229 A1 | 1/2004 | Fulkerson et al. | |
| 2004/0034402 A1 | 2/2004 | Bales et al. | |
| 2004/0044401 A1 | 3/2004 | Bales et al. | |
| 2004/0073290 A1 | 4/2004 | Chouinard | |
| 2004/0073291 A1 | 4/2004 | Brown et al. | |
| 2004/0117002 A1 | 6/2004 | Girton et al. | |
| 2004/0230293 A1 | 11/2004 | Yip et al. | |
| 2004/0236400 A1 | 11/2004 | Edwin et al. | |
| 2004/0236409 A1 * | 11/2004 | Pelton et al. | 623/1.18 |
| 2004/0254637 A1 * | 12/2004 | Yang et al. | 623/1.34 |
| 2005/0049682 A1 | 3/2005 | Leanna et al. | |
| 2005/0060025 A1 | 3/2005 | Mackiewicz et al. | |
| 2005/0149168 A1 | 7/2005 | Gregorich | |
| 2005/0172471 A1 | 8/2005 | Vietmeier | |
| 2005/0182477 A1 | 8/2005 | White | |
| 2005/0222667 A1 | 10/2005 | Hunt | |
| 2005/0278019 A1 * | 12/2005 | Gregorich | 623/1.44 |
| 2006/0030934 A1 | 2/2006 | Hogendijk et al. | |
| 2006/0064153 A1 | 3/2006 | Langhans et al. | |
| 2006/0216431 A1 | 9/2006 | Kerrigan | |
| 2006/0241741 A1 | 10/2006 | Lootz | |
| 2006/0265049 A1 | 11/2006 | Gray et al. | |
| 2007/0112421 A1 | 5/2007 | O'Brien | |
| 2007/0219624 A1 | 9/2007 | Brown et al. | |
| 2008/0051885 A1 | 2/2008 | Llanos et al. | |
| 2008/0188924 A1 | 8/2008 | Prabhu | |
| 2009/0125092 A1 | 5/2009 | McCrea et al. | |
| 2009/0125099 A1 | 5/2009 | Weber et al. | |
| 2009/0200360 A1 * | 8/2009 | Wack | 228/171 |
| 2009/0204201 A1 | 8/2009 | Wack | |
| 2009/0204203 A1 | 8/2009 | Allen et al. | |
| 2009/0264982 A1 * | 10/2009 | Krause et al. | 623/1.15 |
| 2010/0016949 A1 | 1/2010 | Wack | |
| 2010/0114298 A1 | 5/2010 | Dorn et al. | |
| 2010/0191321 A1 | 7/2010 | Schlun et al. | |
| 2010/0204784 A1 * | 8/2010 | Molaei et al. | 623/1.44 |
| 2010/0211161 A1 | 8/2010 | Dreher | |
| 2010/0234936 A1 | 9/2010 | Schlun | |
| 2010/0249903 A1 | 9/2010 | Wack et al. | |
| 2010/0298921 A1 | 11/2010 | Schlun et al. | |
| 2011/0196473 A1 | 8/2011 | McCrea et al. | |
| 2011/0198327 A1 | 8/2011 | Prabhu | |
| 2011/0245905 A1 | 10/2011 | Weber et al. | |
| 2011/0319977 A1 | 12/2011 | Pandelidis et al. | |
| 2012/0041542 A1 | 2/2012 | Lombardi et al. | |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |
| EP | 1157673 A2 | 11/2001 |
| EP | 1190685 A2 | 3/2002 |
| EP | 1212991 A2 | 6/2002 |
| EP | 1245203 A2 | 10/2002 |
| EP | 1255507 A1 | 11/2002 |
| EP | 1356789 A1 | 10/2003 |
| EP | 1433438 A2 | 6/2004 |
| EP | 1488763 A2 | 12/2004 |
| EP | 1767240 A1 | 3/2007 |
| EP | 2134301 A2 | 12/2009 |
| FR | 2626046 A1 | 7/1989 |
| GB | 453944 A | 9/1936 |
| JP | 07315147 A | 12/1995 |
| JP | 2004-506477 A | 3/2004 |
| JP | 2007-504891 A | 3/2007 |
| JP | 4827965 B2 | 11/2011 |
| JP | 4933018 B2 | 5/2012 |
| WO | 9417754 A1 | 8/1994 |
| WO | 9503010 A1 | 2/1995 |
| WO | 9938457 A1 | 8/1995 |
| WO | 9626689 A1 | 9/1996 |
| WO | 9733534 A1 | 9/1997 |
| WO | 9820810 A1 | 5/1998 |
| WO | 9915108 A1 | 1/1999 |
| WO | 9949928 A1 | 10/1999 |

| | | |
|---|---|---|
| WO | 9955253 A1 | 11/1999 |
| WO | 0045742 A1 | 8/2000 |
| WO | 0049971 A1 | 8/2000 |
| WO | 0064375 A1 | 11/2000 |
| WO | 0101889 A1 | 1/2001 |
| WO | 0132102 A1 | 5/2001 |
| WO | 0158384 A1 | 8/2001 |
| WO | 0176508 A2 | 10/2001 |
| WO | 0215820 A2 | 2/2002 |
| WO | WO-0215820 A2 | 2/2002 |
| WO | 0249544 A1 | 6/2002 |
| WO | 03055414 A1 | 7/2003 |
| WO | 03075797 | 9/2003 |
| WO | 03101343 A1 | 12/2003 |
| WO | 2004019820 A1 | 3/2004 |
| WO | 2004028408 A1 | 4/2004 |
| WO | 2004032802 A2 | 4/2004 |
| WO | 2004058384 A1 | 7/2004 |
| WO | 2005067816 A1 | 7/2005 |
| WO | 2005072652 A1 | 8/2005 |
| WO | 2005104991 A1 | 11/2005 |
| WO | 2005032403 A3 | 12/2005 |
| WO | 2006010636 A1 | 2/2006 |
| WO | 2006010638 A1 | 2/2006 |
| WO | 2006014768 A1 | 2/2006 |
| WO | 2006025847 A2 | 3/2006 |
| WO | 2006036912 A2 | 4/2006 |
| WO | 2006047977 A1 | 5/2006 |
| WO | 2006064153 A1 | 6/2006 |
| WO | 2007073413 A1 | 6/2007 |
| WO | 2006026778 A3 | 11/2007 |
| WO | 2007131798 A1 | 11/2007 |
| WO | 2007135090 A1 | 11/2007 |
| WO | 2008006830 A1 | 1/2008 |
| WO | 2008022949 A1 | 2/2008 |
| WO | 2008022950 A1 | 2/2008 |
| WO | 2008025762 A1 | 3/2008 |
| WO | 2008028964 A2 | 3/2008 |
| WO | 2008055980 A1 | 5/2008 |
| WO | 2008101987 A1 | 8/2008 |
| WO | 2008119837 A2 | 10/2008 |
| WO | 2009030748 A2 | 3/2009 |

OTHER PUBLICATIONS

U.S. Appl. No. 10/362,040, filed Jun. 27, 2003 Advisory Action dated Dec. 16, 2010.
U.S. Appl. No. 12/373,116, filed Jul. 14, 2009 Non-Final Office Action dated Nov. 10, 2010.
Database Wikipedia, Sep. 11, 2007, "Lumen (anatomy)" XP 002453737 abstract.
International Application No. PCT/EP2001/009467 International Preliminary Examination Report Sep. 17, 2002.
International Application No. PCT/EP2001/009467 International Search Report dated Feb. 18, 2002.
International Application No. PCT/EP2007/057041 filed Jul. 10, 2007 International Preliminary Report on Patentability dated Jan. 13, 2009.
International Application No. PCT/EP2007/057041 filed Jul. 10, 2007 International Search Report dated Oct. 18, 2007.
International Application No. PCT/EP2007/057041 filed Jul. 10, 2007 Written Opinion Jan. 10, 2009.
International Application No. PCT/EP2007/058416 filed Aug. 14, 2007 International Preliminary Report on Patentability dated Feb. 24, 2009.
International Application No. PCT/EP2007/058416 filed Aug. 14, 2007 International Search Report dated Nov. 22, 2007.
International Application No. PCT/EP2007/058416 filed Aug. 14, 2007 Written Opinion dated Feb. 23, 2009.
International Application No. PCT/EP2008/052121 filed Feb. 21, 2008 International Preliminary Report on Patentability dated Aug. 26, 2009.
International Application No. PCT/EP2008/052121 filed Feb. 21, 2008 International Search Report dated May 19, 2008.
International Application No. PCT/EP2008/052121 filed Feb. 21, 2008 Written Opinion dated May 9, 2008.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Office Action dated Aug. 18, 2008.
U.S. Appl. No. 10/362,040, filed Jun. 27, 2003 Office Action dated Aug. 2, 2006.
U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/438,330, filed Feb. 20, 2009 Office Action dated Mar. 16, 2010.
U.S. Appl. No. 10/362,040, filed Jun. 27, 2003 Final Office Action dated Aug. 30, 2010.
U.S. Appl. No. 12/438,330, filed Feb. 20, 2009 Advisory Action dated Oct. 14, 2010.
U.S. Appl. No. 12/438,330, filed Feb. 20, 2009 Office Action dated Aug. 5, 2010.
Feb. 4, 2008 International Search Report in international application No. PCT/EP2007/063347 filed on Dec. 5, 2007.
Jun. 10, 2009 International Search Report in international application No. PCT/EP2007/063347 filed on Dec. 5, 2007.
Jun. 10, 2009 Written Opinion of the International Search Authority in international application No. PCT/EP2007/063347 filed on Dec. 5, 2007.
U.S. Appl. No. 10/362,040, filed Jun. 27, 2003 Notice of Allowance dated Jun. 22, 2011.
U.S. Appl. No. 12/373,116, filed Jul. 14, 2009 Advisory Action dated Jul. 26, 2011.
U.S. Appl. No. 12/373,116, filed Jul. 14, 2009 Final Office Action dated Apr. 27, 2011.
U.S. Appl. No. 12/438,330, filed Feb. 20, 2009 Office Action dated Mar. 4, 2011.
EP 07787316.4 filed Jul. 10, 2007 Examination Report dated Dec. 23, 2011.
U.S. Appl. No. 12/438,330, filed Feb. 20, 2009 Final Office Action dated Aug. 11, 2011.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,330, filed Feb. 20, 2009 Advisory Action dated Oct. 20, 2011.
U.S. Appl. No. 12/438,330, filed Feb. 20, 2009 Non-Final Office Action dated Jun. 7, 2012.
U.S. Appl. No. 12/528,289, filed Aug. 26, 2009 Non-Final Office Action dated Jan. 27, 2012.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.

PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12. 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Examiner's Answer dated Jan. 3, 2013.
U.S. Appl. No. 12/438,102, filed Feb. 19, 2009 Non-Final Office Action dated Nov. 15, 2010.
U.S. Appl. No. 12/438,330, filed Feb. 20, 2009 Notice of Allowance dated Sep. 25, 2012.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
U.S. Appl. No. 12/594,531, filed Oct. 2, 2009 Non-Final Office Action dated Oct. 2, 2012.
U.S. Appl. No. 13/279,189, filed Oct. 21, 2011 Non-Final Office Action dated Oct. 17, 2012.

* cited by examiner

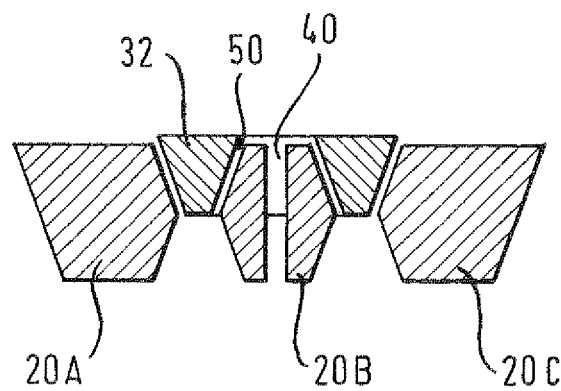
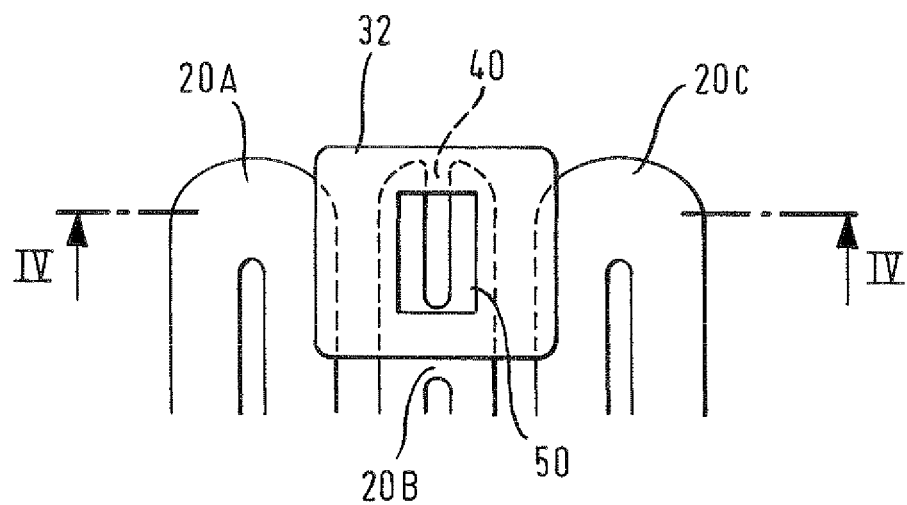

STENTING RING WITH MARKER

PRIORITY

This application is a U.S. national stage application under 35 USC §371 of International Application No. PCT/EP2007/063347, filed Dec. 5, 2007, claiming priority to United Kingdom Patent Application No. 0624419.8, filed Dec. 6, 2006, each of which is incorporated by reference in its entirety into this application.

TECHNICAL FIELD

This invention relates to a stenting ring made of a tube or rolled-up sheet that has a characteristic wall thickness the ring defining a lumen and being equipped with at least one marker made of a material different from that of the ring, the ring being expansible from a radially compact disposition with a relatively small circumference to a radially expanded disposition with a relatively large circumference, the ring exhibiting in the compact disposition a serpentine arrangement of succeeding struts lying in alternate opposite directions to the longitudinal axis of the lumen.

BACKGROUND ART

Stenting rings on the market are made from biologically compatible metals such as stainless steel or nickel-titanium shape memory alloy and, as these materials are relatively poorly visible in x-ray images, they are often equipped with "markers" that are more opaque to x-rays thereby allowing the radiologist to monitor the position of the stent in a bodily lumen. It is advantageous when the radiopaque marker has an electrochemical potential similar to that of the stent metal, thereby to minimise electrochemical corrosion of the prosthesis that includes the stent and the marker. This is one reason why tantalum is a popular choice as radiopaque marker or nickel-titanium shape memory alloy stents.

In designing the marker, compromises are unavoidable. The bigger the marker, the more effectively it reveals to the radiologist the location of the stent. However, the bigger the marker, the more it can interfere with trans-luminal delivery of the stent and, indeed, performance of the stent at the stenting site. One way to accomplish an effective compromise is to provide more or less a complete ring of marker material around the stent lumen, but cantilevered from the stent metal as such, beyond each end of the stent cylinder. Such a prosthesis exhibits, after delivery and deployment, an expanded diameter cylindrical space in which the stent is working and, beyond each end of that stent cylinder, a plurality of radiopaque markers, attached to the stent, and spaced from each other around the circumference of the stenting cylinder. Within the length of the stenting cylinder, gaps between successive stent struts, as one advances around the circumference of the stenting cylinder, are relatively small. Conversely, when one advances around the circumference of the circle in which the spaced radiopaque markers are to be found, the gaps between adjacent markers around the circumference are relatively large.

The purpose of the markers is to inform those operating on the patient where exactly within the patient the stent is located. Markers located at positions cantilevered beyond the ends of the stent cylinder are not ideal, in that they are not precisely coincident with the ends of the stent cylinder.

For marker disclosures see, for example, WO-A-97/33534, WO-A-02/078762 and WO-A-03/101343 as well as EP-A-1212991 and 1356789.

SUMMARY OF THE INVENTION

In accordance with the present invention, the marker has a thickness in the radial direction of the ring that is less than the characteristic wall thickness, and has a width that extends circumferentially around an arc of the ring. The marker is attached to the ring at a zone located at a point intermediate in the extent of said arc. The marker overlaps with a respective one of said struts, at each end of its circumferential arc, when the ring is in the compact disposition, the respective struts moving away from each other, and from the marker, when the ring expands towards said radially expanded disposition.

Those skilled in the art of stent manufacture and use are well aware of the advantages that follow when the annulus that contains the stent construction can be presented with a small radial thickness. Every increment in thickness in the radial extent of the stent annulus is detrimental to the ability of the stent to be transluminally delivered along narrow and tortuous bodily lumens and will require larger sized delivery systems. One problem with reducing the radial thickness of the stent annulus is that stenting force is sacrificed. Stenting force is the force that the stent can bring to bear on bodily tissue at the stenting site which is going to be urged radially outwardly by the stent being placed. One wants a high stenting force but, at the same time, one wants high flexibility from the same stent matrix, so that it can be delivered transluminally along a tortuous lumen and further, in at least some applications, has the flexibility necessary after deployment to perform inside the body at the stenting location without damaging the bodily tissue surrounding it.

Thus, it is not attractive to stent designers to accept any local or global increase of radial thickness to accommodate a marker. A valuable contribution to the art which is made by the present invention is to achieve a good compromise between stent flexibility and stenting force without any local or global increase of the radial thickness, yet at the same time locate relatively large and therefore visible radiopaque markers at positions that provide the radiologist with direct information, in the sense that the radiopaque marker is coincident with that portion of the stent whose location needs to be known with precision (typically the end of the stent cylinder).

The present invention achieves this compromise by using a marker that has a radial thickness less than that of the stenting ring, and overlapping that marker with portions of the stenting ring which are themselves locally of a smaller radial thickness, whereby the radial thickness of the part of the prosthesis that includes both portions of a stenting ring and part of the radiopaque marker are not so thick in a radial direction as the combined radial thickness of the marker and of the sheet from which the stenting ring is formed.

There are a number of ways to create a matrix of stenting struts, that form a stenting ring, from sheet or tube material. One of the most popular is to use a laser to cut slits in the material of the sheet or tube, the remaining material between successive laser-cut slits providing the struts of the stenting ring. With the advent of microprocessor controlled laser cutters, that can change continuously the orientation of the cutting laser beam with respect to the plane of the sheet workpiece or the longitudinal axis of the tubular workpiece, a good range of possibilities is made available to sculpt the cross-section of a stenting ring strut, and constantly modulate it so that it conforms everywhere to the cross-section optimal for its surroundings. For example, using a laser cutter, the cross-section of those struts of a stenting ring that are overlapped by the marker can be of a radial thickness that is less than the thickness of the sheet or tube out of which the stent is being cut by the laser.

In our already published WO2002/015820, it is taught how to take advantage of laser cutting technology applied to a tubular workpiece to enhance the bond between a stent and a marker. The laser naturally produces frusto-conical joining surfaces on the stent and the marker, which can be brought together at an interface between the stent and a marker that is relatively secure and precise. That technology is now known to those skilled in the art, by virtue of the successful LUMINEXX stent that has been on the market for some considerable time. The present invention can therefore be looked upon as an enhancement of LUMINEXX technology.

With ever-increasing performance of laser cutting equipment, dimensional tolerances become ever more refined, allowing an ever more precise "fit" between stent and marker, with deliberate inclusion in the design concept of strain when stent and marker are brought into engagement with each other, by imposing a chosen degree of elastic stress on the material that backs each interface between the stent and a marker thereby to increase the level of assurance that the bond between stent and marker is secure.

It is conventional to electro-polish stent workpieces. Given the significant difference between the metal of the stent and the metal of the marker, it would be convenient to electro-polish separately the stent metal workpiece and the marker. However, electro-polishing can introduce a degree of uncertainty as to the precise dimensions of the electro-polished workpiece. For optimal bonding between stents and markers, precise control of dimensions is needed, which would appear to stand in the way of electro-polishing before joining together the stent metal and the marker metal. However, if the components to be joined at the interface are designed on the basis that elastic strain is to compensate for the degree of uncertainty as to dimensions for which separate electro-polishing of the two components is responsible, then separate electro-polishing ought not to prejudice the objective of precise and safe joining of markers to stent material.

For a better understanding of the present invention and, to show more clearly how the same can be carried onto effect, reference will now be made, by way of example, to the accompanying drawings.

BRIEF DESCRIPTION OF THE DRAWINGS

FIG. 4 is a cross-section through part of one end of a stent and marker; and

FIG. 5 is a view of the stent part shown in section in FIG. 4, with the section line marked IV-IV.

DETAILED DESCRIPTION

Figure 1:
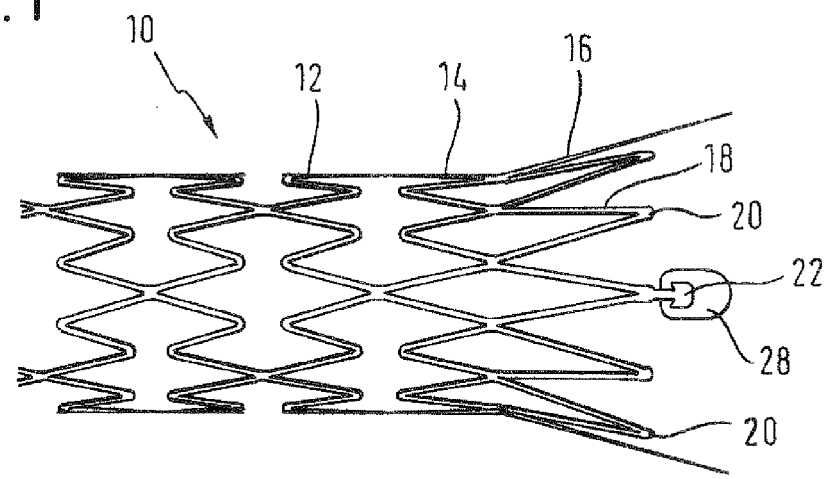
FIG. 1 is a view from one side of one end of a stent, showing a marker.

Looking first at FIG. 1, this is part of a drawing taken from applicant's WO 02/15820 and the reader is referred to that WO document for a detailed description of the content of the Figure. A self-expanding stent 10 of nickel-titanium shape memory alloy exhibits zig-zag stenting rings, such as 12 and 14, that are shown in FIG. 1 in an expanded configuration, after deployment in bodily tissue. The end ring 16 has longer struts 18 than our present inner rings 12 and 14 and, where two end struts 18 come together at nodes 20 is the axial extent of the stent lumen. Cantilevered from just 4 of the 12 end nodes 20, on a carrier portion 22, is a radiopaque tantalum marker spoon 28. As explained in the WO document, when the stent 10 is in the radially compact delivery disposition, the ring of 4 tantalum marker spoons 28 cantilevered on the end of the stent forms virtually a full circle of tantalum metal in the catheter delivery system for the stent, rendering it relatively easy for the radiologist to track the progress of the stent in the body before it is deployed.

However, the location of the tantalum spoons 28 is beyond the axial extent 20 of the stent 10.

Figure 2:
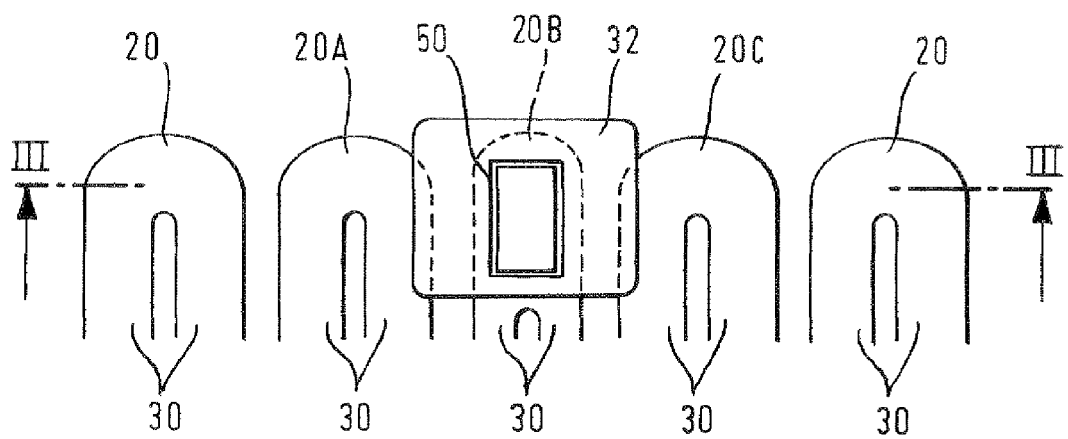
FIG. 2 is a view of part of one end of a stent, again showing a marker.

Turning to FIG. 2, and using identical reference numbers when feasible, the view shows part of the end of a stent, again indicated by the end nodes 20 at the junction of respective struts 30 of the terminal zig-zag stenting ring of the stent. The drawing shows a marker panel 32 but that marker overlies radially part of the terminal zig-zag ring, fully covering node 20B and partly covering nodes 20A and 20C. The marker panel 32 is attached to the central node 20B. In order to facilitate this attachment, the node 20B to which the marker panel is attached is axially extended as compared to other nodes. Another way of looking at this is to say that the struts 30 coming together to form the node 20B to which the marker 32 is attached are axially shortened. Although FIG. 2 shows only one marker, readers will appreciate that a plurality of markers could be provided, around the circumference of the end of the stent, comparable with the FIG. 1 scheme of markers, to provide more or less a complete ring of radiopaque material when the stent is in the radially compressed configuration (as depicted in FIG. 2). The marker panels 32 are conveniently cut from a tubular workpiece with a fitting radius and wall thickness. As can be seen, the axial end of the marker 32 is coterminous with the axial end of the stent 10. In fact, with the stent 10 and marker 32 combination of the present invention, markers 32 can even be provided at positions between the axial ends of the stent 10 in applications where this is desirable, with minimal increase in the radial thickness made to the stent 10.

Figure 3:
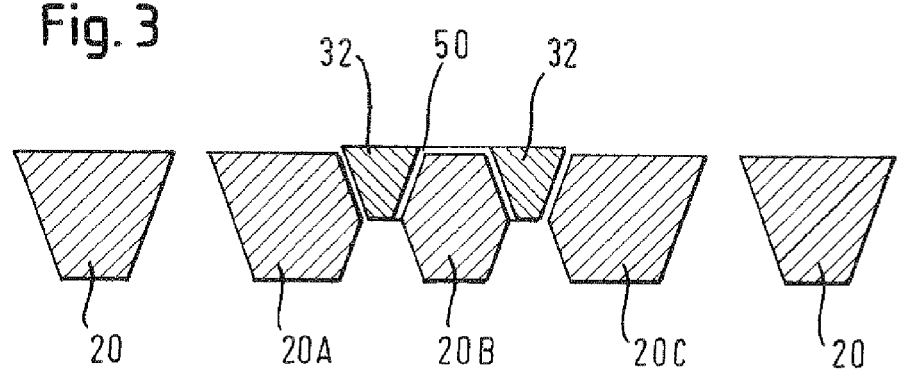
FIG. 3 is a cross-section along the line III-III in FIG. 2.

Turning to FIG. 3, it is revealed how the nodes 20 can be laser cut, and the marker panel 32, so as to make the space available to fit the marker panel 32 between the adjacent nodes 20A, B and C. In the shown configuration, the marker panel 32 has two frusto-conical radially extending portions. The radially extending portions include side surfaces that taper towards one another from an outer surface of the marker panel 32 to an inner surface of the marker panel. The three adjacent nodes 20A, 20B and 20C include surfaces generally mating with the side surfaces of the marker panel 32. Thus, the frusto-conical portions of the marker panel 32 can extend into the thickness of the stent 10 by cutting a space in the three adjacent nodes 20A, 20B and 20C of the stent to provide mating surfaces. Such an arrangement allows a marker panel to be well supported by the stent 10 and the marker panel 32 can be positioned at a desired position overlying the stent with minimal increase in thickness of the stent 10.

The use of tapering side surfaces in the marker panel 32 is advantageous as it allows the mating surfaces in the stent 10 to be laser cut. In particular, a laser cutting method is used where the laser passes through the stent 10 along a line that is offset from the longitudinal axis of the stent. The laser can thus cut corners off the stent struts at appropriate positions to provide spaces to matingly receive the marker panel 32. Perpendicular mating surfaces would offer good support, but would not be so readily implemented with a laser cutting method. The tapered surfaces of the stent 10 upon which the mating surfaces of the marker panel 32 can rest, as shown in FIG. 3, provide a solution where the stent 10 supports the marker 32 and where off-axis laser cutting can be used to produce them.

The marker panel 32 can be welded into position. In the embodiment shown in FIG. 2, the marker panel 32 is welded to the mating surfaces of the central node 20B, while the mating surfaces of the outer nodes 20A and 20C provide space for the circumferential extension of the marker, but without hindering radial expansion of the outer nodes 20A and 20C from the central node 20B. The marker 32 includes a hole 50 into which welding material can be introduced. The shaded box around the hole 50 represents the welding material attaching the mating surfaces of the marker 32 and the central node 20B.

The skilled reader can think of other joining techniques apart from welding such as gluing, pinning, latching, strapping and encapsulating.

FIG. 4 shows a variant. By providing node 20B with a slit 40, it can be arranged that the fit between marker 32 and node 20B has a degree of resilient elastic strain corresponding to a squeezing of the slit walls towards each other when the marker 32 is pressed over the node 20B. This is helpful, for accommodation of manufacturing tolerances. Electro-polishing prior to assembly of stent and marker can increase the extent to which component dimensions vary.

FIG. 5 is a view of the fragment shown in section in FIG. 4. As in FIG. 2, the marker panel overlies the nodes 20A, B and C and has two major surfaces that are part of a cylinder with a radius and wall thickness proportionate to that of the stent, the wall thickness being, in general, less than the wall thickness of the workpiece from which the stent strut matrix is created.

As with FIGS. 1, 2 and 3, welding is a preferred way to attach the marker panel to the stent matrix but the other joining techniques mentioned above are also available.

The illustrated embodiments are exemplary and not to be taken as limiting. The claims which follow are what define the inventive concept.

The invention claimed is:

1. A stenting ring made of a tube or rolled-up sheet that has a wall with a characteristic wall thickness, the ring defining a lumen and being equipped with at least one marker made of a material different from a material of the ring, the ring being expansible from a radially compact disposition with a relatively small circumference to a radially expanded disposition with a relatively large circumference, the ring exhibiting in the compact disposition an arrangement of succeeding struts lying in alternate opposite directions, wherein the at least one marker:
    has a thickness in the radial direction of the ring that is less than the characteristic wall thickness, and has a width that extends circumferentially around an arc of the ring,
    includes a hole into which attachment material is introduced to attach the marker to the ring,
    is attached to the ring at a zone located at a point intermediate in an extent of said arc to a node connecting two struts, the node axially extended compared to other nodes in the ring, and
    at least partially radially overlaps with at least one strut adjacent to the arc when the ring is in the compact disposition, the at least one strut moving away from the at least one marker, when the ring expands toward said radially expanded disposition.

2. The stenting ring according to claim 1, wherein a gap exists between outer surfaces of the arc and the at least one strut, and the overlap is such that the at least one marker extends across the gap to at least partially overlie the at least one strut when viewed from outside the ring.

3. The stenting ring according to 1, wherein the at least one marker is located at one end of the lumen.

4. The stenting ring according to claim 1, wherein the at least one marker is located at an intermediate point between opposite ends of the lumen.

5. The stenting ring according to claim 1, wherein the at least one marker is attached to the ring by weld metal.

6. The stenting ring according to claim 1 wherein the at least one marker is attached to the ring at a form-fitting interface.

7. The stenting ring according to claim 1, wherein the at least one marker is attached to the ring at an attachment interface backed by ring and marker material exhibiting elastic strain.

8. The stenting ring according to claim 1, wherein the at least one marker includes radially extending portions, each radially extending portion tapering as it extends toward a longitudinal axis of the stenting ring, and wherein the node to which the at least one marker is attached and the at least one of the two struts include mating surfaces so that the radially extending portions can extend into the wall of the stenting ring.

9. A stent, comprising:
    a plurality of stenting rings including inner stenting rings and an end stenting ring, the end stenting ring including a plurality of nodes, each node formed by two struts joined together at an end thereof, the struts forming the nodes lying adjacent one another generally parallel with a longitudinal axis of the stent stent radially compact configuration; and
    a marker attached to a marker node, the marker node axially extended relative to nodes adjacent thereto, the marker having a thickness in a radial direction of the end stenting ring that is less than a wall thickness of the end stenting ring, the marker positioned at least partially in a gap between outer surfaces of the marker node and at least one adjacent node, the marker at least partially radially overlapping the at least one adjacent node in the stent radially compact configuration, and the marker including a hole positioned over the marker node into which attachment material is introduced.

10. The stent according to claim 9, wherein the struts of the end stenting ring are longer than struts of the inner stenting rings.

11. The stent according to claim 9, wherein the inner stenting rings exhibit a matrix of struts with a characteristic pattern different from a characteristic pattern of the end stenting ring.

12. The stent according to claim 9, wherein the stent, apart from the end stenting ring, has a pattern that is in the form of a helix that winds around the longitudinal axis of the stent.

13. The stent according to claim 9, wherein the marker includes two frusto-conical radially extending portions, each of the portions including side surfaces that taper toward one another from an outer surface of the marker to an inner surface thereof.

14. The stent according to claim 13, wherein the marker node and the nodes adjacent thereto include surfaces generally mating with the tapered side surfaces of the marker radially extending portions.

15. The stent according to claim 9, wherein the marker node includes a slit extending axially along the longitudinal axis of the stent.

16. A stenting ring made of a tube or rolled-up sheet that has a wall with a characteristic wall thickness, the ring defining a lumen and being equipped with at least one marker made of a material different from a material of the ring, the ring being expansible from a radially compact disposition with a relatively small circumference to a radially expanded disposition with a relatively large circumference, the ring exhibiting in the compact disposition an arrangement of succeeding struts lying in alternate opposite directions, wherein the at least one marker:

has a thickness in the radial direction of the ring that is less than the characteristic wall thickness, and has a width that extends circumferentially around an arc of the ring, includes radially extending portions, each radially extending portion tapering as it extends toward a :longitudinal axis of the stenting ring, is attached at a node connecting two struts, wherein the node and at least one of the two struts include surfaces mating with at least one of the radially extending portions, is attached to the ring at a zone located at a point intermediate in an extent of said arc, and at least partially radially overlaps with at least one strut adjacent to the arc when the ring is in the compact disposition, the at least one strut moving away from the at least one marker, when the ring expands toward said radially expanded disposition.

\* \* \* \* \*